United States Patent
Mostafavi et al.

(10) Patent No.: US 8,417,315 B2
(45) Date of Patent: Apr. 9, 2013

(54) MARKER SYSTEMS WITH SPACED APART SURFACES OR MARKERS AND METHODS OF USING THE SAME

(75) Inventors: Hassan Mostafavi, Los Altos, CA (US);
Andrew G. Jeung, Mountain View, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 974 days.

(21) Appl. No.: 11/748,406

(22) Filed: May 14, 2007

(65) Prior Publication Data

US 2008/0287728 A1    Nov. 20, 2008

(51) Int. Cl.
*A61B 5/05*    (2006.01)

(52) U.S. Cl.
USPC ............ 600/407; 600/414; 600/426; 600/476

(58) Field of Classification Search .................. 600/174, 600/414, 426, 428; 250/370.08–370.1
See application file for complete search history.

(56) References Cited

U.S. PATENT DOCUMENTS

| | | | |
|---|---|---|---|
| 6,888,919 B2 | 5/2005 | Graf | |
| 6,973,202 B2* | 12/2005 | Mostafavi | 382/103 |
| 2005/0084073 A1 | 4/2005 | Seppi et al. | |
| 2006/0072706 A1* | 4/2006 | Russell | 378/162 |
| 2007/0014391 A1 | 1/2007 | Mostafavi et al. | |

FOREIGN PATENT DOCUMENTS

| | | |
|---|---|---|
| JP | 2005-111115 A | 4/2005 |
| WO | 99/27839 | 6/1999 |
| WO | 9927839 | 6/1999 |

OTHER PUBLICATIONS

Supplementary European Search Report dated Apr. 28, 2010 for EP Application No. 08747676.8.
International Search Report mailed Jul. 14, 2008 for Application No. PCT/US2008/62727.
Written Opinion mailed Jul. 14, 2008 for Application No. PCT/US2008/62727.
Extended EP Search Report for EP 08747676.8.
European Examination Report dated Mar. 2, 2012 for EP Patent Application No. 08747676.8.
Notice of Reasons for Rejection dated Oct. 23, 2012 for Japanese Patent Application No. 2010-508495.

* cited by examiner

*Primary Examiner* — Parikha Mehta
(74) *Attorney, Agent, or Firm* — Vista IP Law Group, LLP (57) ABSTRACT

A marker system includes a structure having a first surface and a second surface, a first marker located on the first surface, and a second marker located on the second surface, wherein the first marker and the second marker are arranged so that they face approximately a same direction, and so that they can be simultaneously viewed by an optical device, and wherein a first distance between the first marker and the optical device is different from a second distance between the second marker and the optical device when the first and the second markers are simultaneously viewed by the optical device.

42 Claims, 7 Drawing Sheets

MARKER SYSTEMS WITH SPACED APART SURFACES OR MARKERS AND METHODS OF USING THE SAME

FIELD

This application relates to marker systems, and more specifically, to marker systems for use in the medical field.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Normal physiological movement represents a limitation in the clinical planning and delivery of conventional radiotherapy and conformal therapy. Normal physiological movement, such as respiration or heart movement, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

To address this problem, the size and/or shape of the radiation beam can be expanded by a "movement margin" (i.e., the predicted movement distance in any direction of the targeted tumor) to maintain full irradiation of the targeted tissue. The drawback to this approach is that this increased irradiation volume results in radiation being applied to otherwise healthy tissue that is located within the area of the expanded volume. In other words, motion during treatment necessitates the application of a radiation field of an expanded size that could negatively affect an unacceptably large volume of normal tissue surrounding the targeted treatment volume.

Another approach to this problem involves physiological gating of the radiation beam during treatment, with the gating signal synchronized to the movement of the patient's body. In this approach, instruments are utilized to measure the physiological state of the patient with reference to the particular physiological movement being examined. For example, respiration has been shown to cause movements in the position of a lung tumor in a patient's body. If radiotherapy is being applied to the lung tumor, then a temperature sensor, strain gauge or preumotactrograph can be attached to the patient to measure the patient's respiration cycle. The radiation beam can be gated based upon certain threshold points within the measured respiratory cycle, such that the radiation beam is disengaged during periods in the respiration cycle that correspond to excessive movement of the lung tumor.

Currently, there is a need for a method and system that can accurately and consistently allow for execution of physiological gating of radiation application.

SUMMARY

In accordance with some embodiments, a marker system includes a structure having a first surface and a second surface, a first marker located on the first surface, and a second marker located on the second surface, wherein the first marker and the second marker are arranged so that they face approximately a same direction, and so that they can be simultaneously viewed by an optical device, and wherein a first distance between the first marker and the optical device is different from a second distance between the second marker and the optical device when the first and the second markers are simultaneously viewed by the optical device.

In accordance with other embodiments, a marker system that includes a structure having a base, a first surface, and a second surface, the first surface forming an angle with the base, the angle being a value that is between 30° and 90°, a first marker located on the first surface, and a second marker located on the second surface, wherein the first surface has a planar region, the planar region having an area that is larger than an area covered by the first marker.

In accordance with other embodiments, a method of using a marker system having an optical device that includes placing a first marker at a first position, and placing a second marker at a second position, wherein the first marker and the second marker are placed such that a distance between the first marker and the second marker measured in a viewing direction of the optical device is at least 0.5 centimeter.

In accordance with other embodiments, a marker system that includes a first marker having a first normal, and a second marker having a second normal, wherein the first normal and the second normal form an angle that is less than 15°, and the second marker is spaced from a plane that is perpendicular to the first normal and that intersects the first marker.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments.

Radiation System

Figure 1:
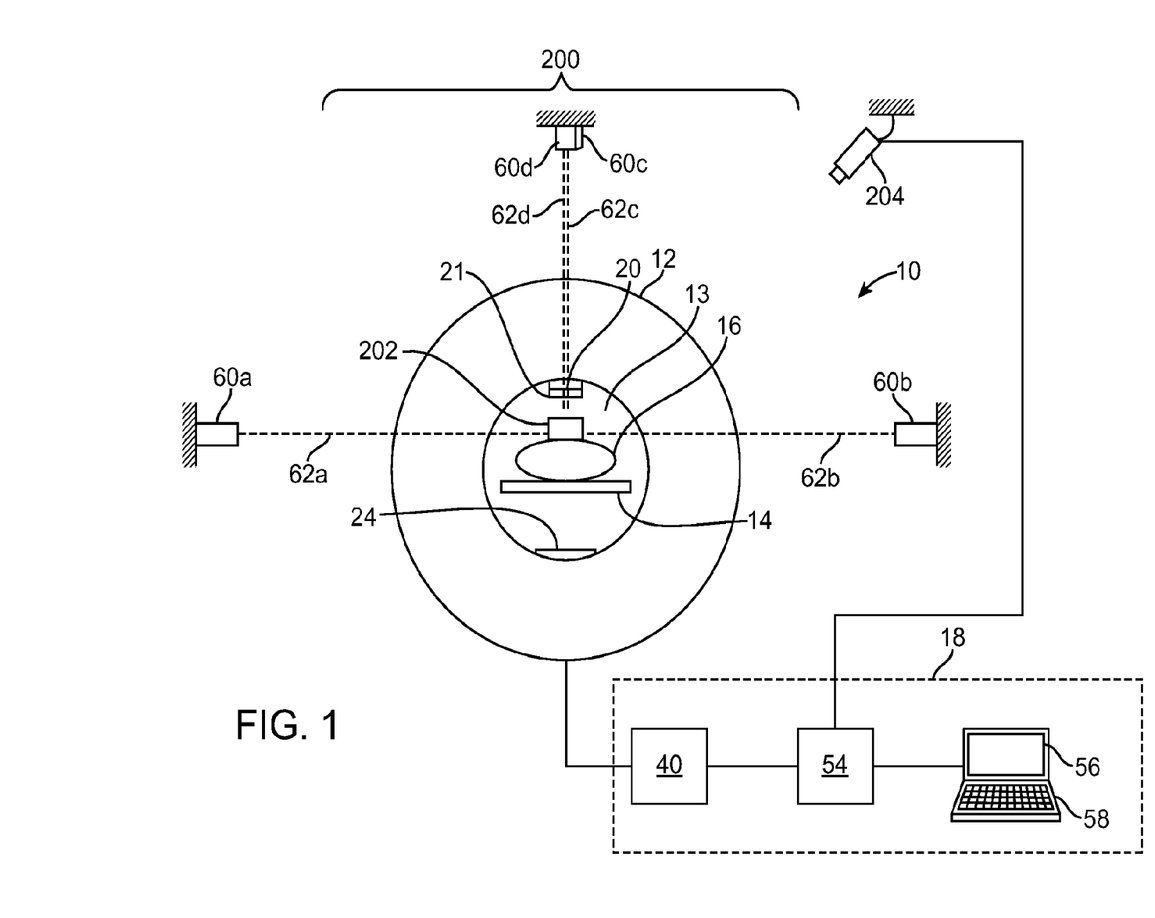
FIG. 1 illustrates a radiation system with which embodiments of marker systems described herein may be used.

FIG. 1 illustrates a radiation system 10. The system 10 includes a gantry 12 having an opening (or bore) 13, a patient support 14 for supporting a patient 16, and a control system 18 for controlling an operation of the gantry 12. In the illustrated embodiments, the gantry 12 has a slip-ring configuration (donut shape). Alternatively, the gantry 12 can have other configurations, such as a C-arm configuration. The system 10 also includes a radiation source (e.g., x-ray source) 20 that projects a beam of radiation towards the patient 16, and a collimator 21 for changing a shape of the beam. The system 10 also includes a detector 24 on an opposite side of the gantry 12, which in some cases, may be used to receive radiation exiting from the patient 16, and generate image(s) using the received radiation. The detector 24 has a plurality of sensor elements configured for sensing a x-ray that passes through the patient 16. Each sensor element generates an electrical signal representative of an intensity of the x-ray beam as it passes through the patient 16. In other embodiments, the system 10 does not include the detector 24.

In the illustrated embodiments, the radiation source 20 is a treatment radiation source for providing treatment energy. In other embodiments, the radiation source 20 may be a diagnostic radiation source for providing diagnostic energy (e.g., energy that is suitable for generating an image). In further embodiments, the radiation source 20 can be configured to selectively provide treatment energy and diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIO-THERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003.

The control system 18 includes a processor 54, such as a computer processor, coupled to a source rotation control 40. The control system 18 may also include a monitor 56 for displaying data and an input device 58, such as a keyboard or a mouse, for inputting data. During a scan to acquire x-ray projection data (e.g., cone beam CT image data), the source 20 rotates about the patient 16. The rotation of the source 20 and the operation of the radiation source 20 are controlled by the source rotation control 40, which provides power and timing signals to the radiation source 20 and controls a rotational speed and position of the source 20 based on signals received from the processor 54. Although the control 40 is shown as a separate component from the gantry 12 and the processor 54, in alternative embodiments, the control 40 can be a part of the gantry 12 or the processor 54.

During a radiation procedure, the radiation source 20 generates and directs an x-ray beam towards the patient 16, while the detector 24 measures the x-ray absorption at a plurality of transmission paths defined by the x-ray beam during the process. The detector 24 produces a voltage proportional to the intensity of incident x-rays, and the voltage is read and digitized for subsequent processing in a computer. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning.

As shown in the figure, the radiation system 10 is used with a marker system 200 that includes a marker block 200 and a camera 204. The camera 204 is coupled to the processor 54, which in accordance with some embodiments, may be a part of the marker system 200. Alternatively, instead of the processor 54, the camera 204 may be coupled to another processor (not shown). Also, in other embodiments, the marker system 200 may not include the camera 204. During use, the marker block 202 is coupled to the patient 16 (e.g., placed on the patient's chest, abdomen, or another body part), and the camera 204 is used to view the marker block 202. The camera 204 transmits image data to the processor 504, which processes the image data to determine a position and/or orientation of the marker block 202.

As shown in the figure, four lasers 60a-60d are positioned adjacent to the system 10. The lasers 60a-60d are configured to generate respective laser beams 62a-62d, which may be used to align the marker block 202 (and therefore, the patient 16) at a desired location. In the illustrated embodiments, lasers 60a, 60b are configured to generate and project laser beams 62a, 62b from opposite sides of the marker block 202, laser 60c is configured to generate and project laser beam 62c from above the marker block 202, and laser 60d is configured to generate and project laser beam 62d downwardly at an angle onto the marker block 202. In other embodiments, the lasers 60 may be configured to project the laser beams 62 from other directions. Each laser 60 may be mounted to any structure, such as a wall, a ceiling, a patient support, or another device. Although four lasers 60 are shown, in other embodiments, more or less than four lasers 60 may be used. For example, in other embodiments, only lasers 60a-60c are used.

Marker System

Figure 2:
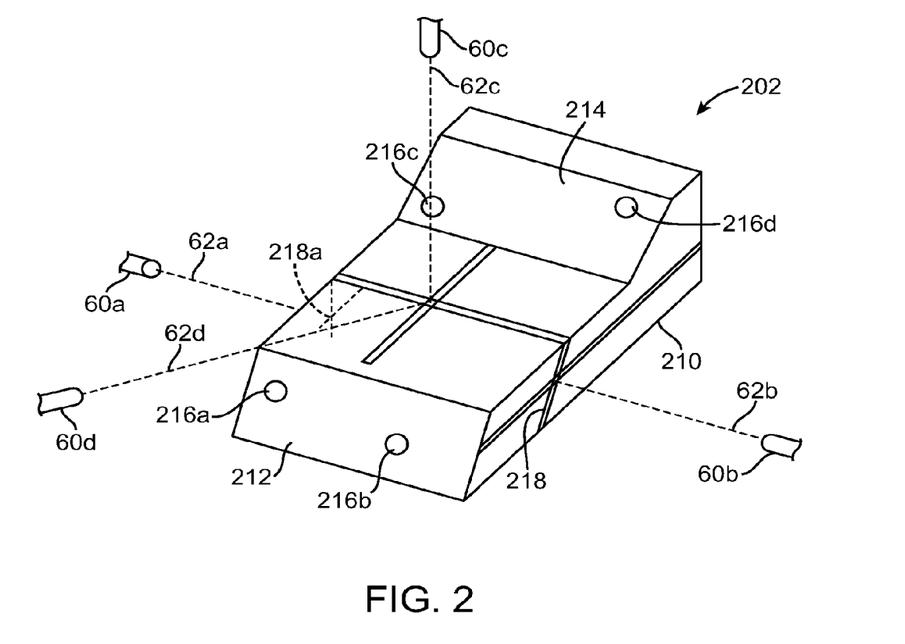
FIG. 2 illustrates an example of a marker block in accordance with some embodiments.

FIG. 2 illustrates the marker block 202 of FIG. 1 in accordance with some embodiments. The marker block 202 includes a structure 210 having a first surface 212 and a second surface 214, and a plurality of markers 216. The structure 210 can be made from a plastic (e.g., a light weight plastic), or any of other materials. In the illustrated embodiments, the marker block 202 includes four markers 216a-216d, wherein markers 216a, 216b are located on the first surface 212, and markers 216c, 216d are located on the second surface 214. In other embodiments, the marker block 202 may include less than four markers or more than four markers. Also, in other embodiments, the distribution of the markers 216 may be different from that shown in the figure. For example, in other embodiments, the marker 216a may be located on the first surface 212, and markers 216b-216d may be located on the second surface 214.

As shown in the figure, each of the markers 216 has a circular shape. In other embodiments, each of the markers 216 can have any of other shapes, such as a square, a rectangular, a triangular, an elliptical, or a customized shape. In further embodiments, instead of the markers 216 having the same shape, one or more markers 216 can have a shape that is different from the rest of the markers 216. The markers 216 are made from a reflective material such that they can be "seen" by the camera 204.

In the illustrated embodiments, the marker block 202 also includes markings 218a-218c. The markings 218 may be depressions located on the surface of the marker block 202. Alternatively, the markings 218 may be paint or materials (e.g., polymers) deposited on the surface of the marker block 202. During use, the markings 218 are used to align the marker block 202 with laser beams 62, thereby allowing the marker block 202 to be placed at a prescribed position and orientation. In particular, the marking 218a provides a target associated with laser beam 62a, the marking 218b provides a target associated with laser beam 62b, and marking 218c provides a target associated with laser beams 62c, 62d.

Figure 3A:
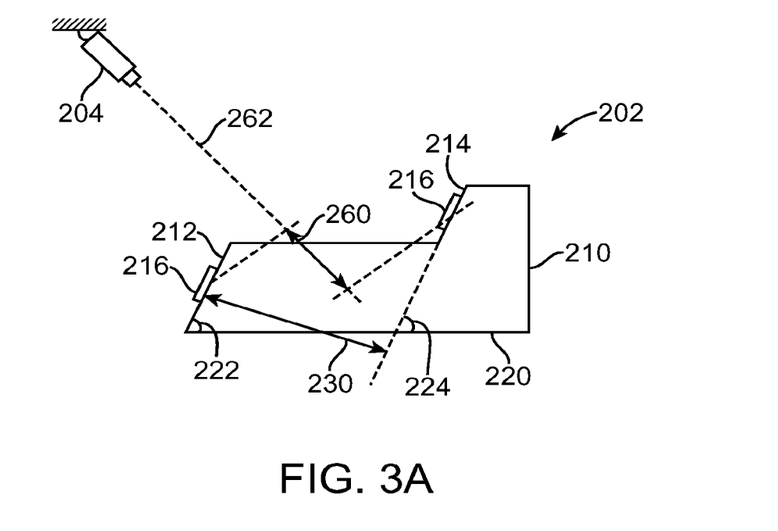
FIG. 3A illustrates a side view of the marker block of FIG. 2 in accordance with some embodiments.

FIG. 3A illustrates a side view of the marker block 202 of FIG. 2 in accordance with some embodiments. As shown in the figure, the first and second surfaces 212, 214 of the structure 210 are inclined relative to a base 220 of the structure 210. This provides a larger surface area (as compared to the case when the surfaces 212, 214 are perpendicular to the base 220) of each marker 216 for the camera 204 to detect. In some embodiments, the surfaces 212, 214 may form respective angles 222, 224 with the base 220, wherein each of the angles 222, 224 may be a value that is between 30° and 90°. In other embodiments, the angles 222, 224 may have other values, depending on the position of the camera 204 relative to the marker block 202. For example, the angles 222, 224 may be selected based on the elevation E of the camera 204 relative to the marker block 202, and a horizontal separation H between the camera 204 and the marker block 202 (e.g., angle $222=90°-\tan^{-1}(E/H)$).

As shown in FIG. 3A, the surfaces 212, 214 are parallel to each other. In the embodiments in which the markers 216 have the same shape, such configuration would result in the images of the markers 216 having the same shape as they appear in an image frame generated by the camera 204. Also, as shown in the figure, the surfaces 212, 214 are spaced apart from each other. In some embodiments, the perpendicular spacing 230 between the surfaces 212, 214 may be a value that is at least 0.5 centimeter, and more preferably at least 1.0 centimeter (e.g., 3 centimeters). In other embodiments, the spacing 230 may have different values.

Figure 3B:
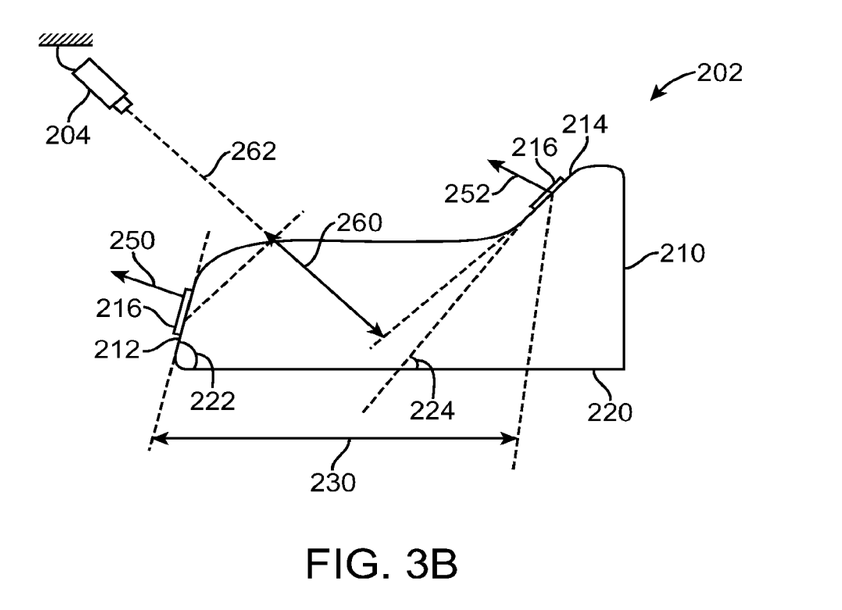
FIG. 3B illustrates a side view of the marker block of FIG. 2 in accordance with other embodiments.

In alternative embodiments, the surfaces 212, 214 may not be parallel, and may instead form an angle relative to each other. FIG. 3B illustrates a variation of the marker block 202 in which a first normal 250 of the first surface 212 and a second normal 252 of the second surface 214 form an angle 254. The angle 254 may be a value that is greater than 0° and less than 45°, and more preferably less than 25°. In other embodiments, the angle 254 can have other values. As shown in the figure, the first and second surfaces 212, 214 are spaced by a distance 230.

In some embodiments, the camera 204 is so positioned relative to the marker block 202 such that a spacing 260 between the first and second surfaces 212, 214 (and therefore, between a marker 216 on the first surface 212 and another marker 216 on the second surface 214) measured in the viewing direction 262 of the camera 204 is a value that is at least 0.5 centimeter, and more preferably at least 1.0 centimeter (e.g., 3 centimeters). In some cases, the value of the spacing 260 may be the same as the value of the spacing 230. In other cases, the value of the spacing 260 may be different from the value of the spacing 230.

The marker block 202 with markers 216 on multiple planes 212, 214 is advantageous because changes in rotation of the marker block 202 can be more easily detected by the single camera 204 than markers on a single rectilinear plane. For any rotation of the marker block 202 (except about the camera axis), the markers 216 in the plane (e.g., plane 212) closer to the camera 204 will move over a larger angle as seen by the camera 204 than the markers 216 in the plane (e.g., plane 214) farther away form the camera 204. Therefore, the tracking system can be much more sensitive to changes in rotation than with a single-plane marker block, in which all the markers will move approximately over the same angle for a given rotation. By placing markers 216 on at least two different planes 212, 214 of the marker block 202, the normals of the markers 216 themselves can point approximately towards a same direction (e.g., towards the camera 204), while still being at different depths away from the camera 204. In some embodiments, two markers 216 are considered as facing approximately a same direction when the respective directions in which the two respective markers 216 face do not vary by more than 30°, and more preferably, do not vary by more than 15°.

Figure 8:
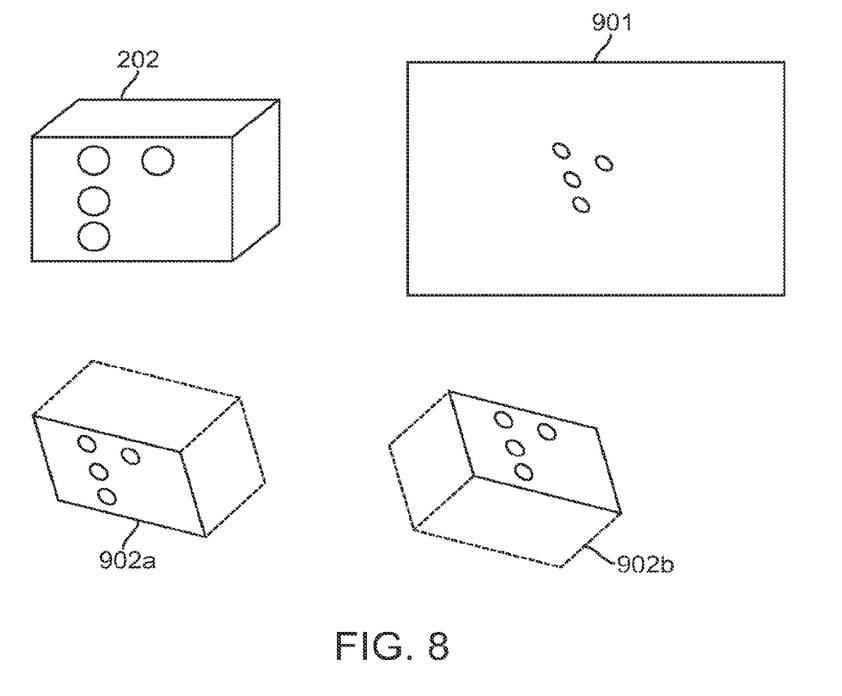
FIG. 8 illustrates an example of a marker block having markers on a common rectilinear plane.

Furthermore, the marker block 202 with markers 216 on multiple planes 212, 214 avoids a certain ambiguity that is present for marker blocks with all markers on one rectilinear plane. FIG. 8 illustrates such principle. Given a marker block 202, the camera 204 will form an image 901 of the markers as seen by the camera 204. Note that given the image 901, the orientation of the block could be interpreted two different ways 902a, 902b. Thus the available image 901 results in an ambiguity in the position of the marker block 202. The multiple plane maker block 202 avoids this ambiguity because the relationship between the two planes in the image will be different depending on the orientation of the structure 210. Therefore the ambiguity illustrated in the example of FIG. 8 is avoided.

Figure 4A:
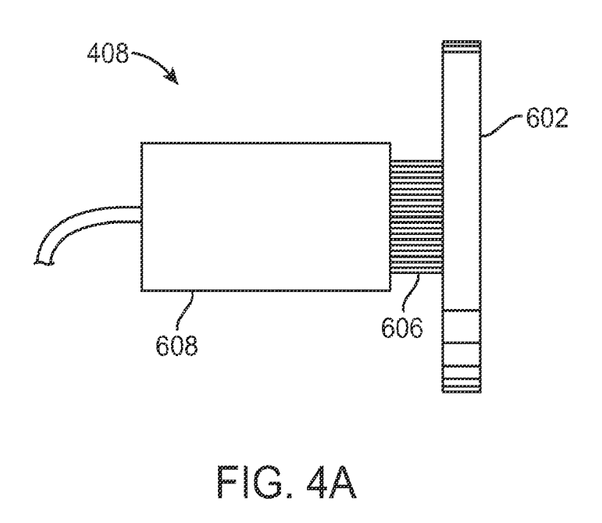
FIG. 4A is a side view of a camera.
Figure 4B:
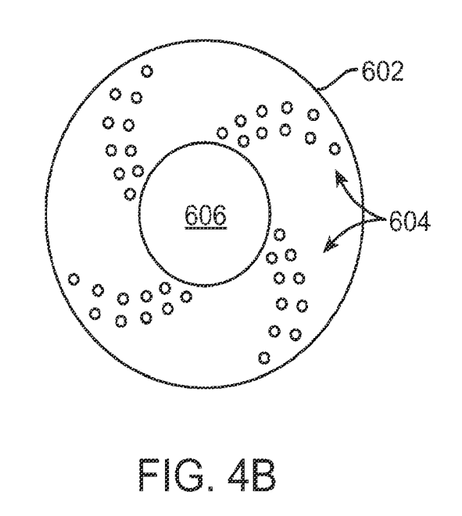
FIG. 4B is a front view of the camera of FIG. 4A.

FIGS. 4A and 4B depict an embodiment of a camera 408. The camera 408 may be an example of the camera 204 shown in FIG. 1. Camera 408 is a charge-couple device ("CCD") camera having one or more photoelectric cathodes and one or more CCD devices. A CCD device is a semiconductor device that can store charge in local areas, and upon appropriate control signals, transfers that charge to a readout point. When light photons from the scene to be images are focused on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to computer 410 to process the video image and to calculate the positions of the retro-reflective markers 406. According to some embodiments, camera 408 is a monochrome CCD camera having RS-170 output and 640×480 pixel resolution. Alternatively, camera 408 can comprise a CCD camera having CCIR output and 756.times.567 pixel resolution.

In the illustrated embodiments, an infra-red illuminator 602 ("IR illuminator") is co-located with camera 408. IR illuminator 602 produces one or more beams of infrared light that is directed in the same direction as camera 408. IR illuminator 602 comprises a surface that is ringed around the lens 606 of camera body 608. The surface of IR illuminator 602 contains a plurality of individual LED elements 604 for producing infrared light. The LED elements 604 are arranged in a spiral pattern on the IR illuminator 602. In other embodiments, the LED elements 604 may be arranged in other patterns. Infrared filters that may be part of the camera 408 are removed or disabled to increase the camera's sensitivity to infrared light.

In operation, one or more illumination sources (which are infrared sources in the preferred embodiment) project light at the patient 16 on patient support 14. The generated light is reflected from markers 216, thereby indicating the position of these markers 216. The camera 204, which is directed at patient 16, capture and detect the reflected light from the markers 216. The camera 204 generates video images that show the position of the markers 216 within its video frame. The generated video images are sent to processor 54 (or another processor) for further processing.

The processor 54 (or another processor) receives video images from the camera 204. The processor 54 first processes each video image from the camera 204 to identify images of the markers 216 in the image frame. Based on the determined position of the markers 216, and the known relative positions among the markers 216, the processor 54 then determines the position (X, Y, Z) and/or orientation ($\theta_x$, $\theta_y$, $\theta_z$) of the marker block 202. In some embodiments, information regarding the location and orientation of the camera 204 is provided to the processor 54 to facilitate the computations of the position and/or orientation of the marker block 202.

A possible inefficiency in tracking the markers 216 is that the markers 216 may appear anywhere on the video frame, and all of the image elements of the video frame may have to be examined to determine the location of the markers 216. Thus, in an embodiment, the initial determination of locations for the markers 216 involves an examination of all of the image elements in the video frame. If the video frame comprise 640 by 480 image elements, then all 307200 (640*480) image elements are initially examined to find the location of the markers 216.

For real-time tracking of the markers 216, examining every image element for every video frame to determine the location of the markers 216 in real-time could consume a significant amount of system resources. Thus, in an embodiment, the real-time tracking of the markers 216 can be facilitated by processing a small region of the video frame, referred to herein as "tracking gate", that is placed based on estimation of the locations of the already-identified markers 216 in the video frame. The previously determined location of a marker 216 is used to define an initial search range (i.e., the tracking gate) for that same marker in real-time. The tracking gate is a relatively small portion of the video frame that is centered at the previous location of the marker 216. The tracking gate is expanded only if it does not contain the new location of the marker 216. As an example, consider the situation when the previously determined location of a particular marker is image element (50,50) in a video frame. If the tracking gate is limited to a 50 by 50 area of the video frame, then the tracking gate for this example would comprise the image elements bound within the area defined by the coordinates (25,50), (75,50), (50,25), and (50,75). The other portions of the video frame are searched only if the marker 216 is not found within this tracking gate.

In some embodiments, the determined position and/or orientation of the marker block 202 can then be used to position the patient 16 at desired position and/or orientation. For example, the determined position of the marker block 202 may be compared with a prescribed position of the marker block 202. In such cases, if the determined position of the marker block 202 matches with the prescribed position, the patient 16 is then considered to be correctly positioned. On the other hand, if the determined position of the marker block 202 does not match the prescribed position, the patient 16 is then positioned (e.g., by moving the patient support 14) until the marker block 202 position matches with the prescribed position.

In other embodiments, the determined position and/or orientation of the marker block 202 can be used to determine the position of at least a portion of the patient 16. In such cases, the relative spatial relationship between the marker block 202 and the patient 16 is known or predetermined. As such, once the marker block 202 position is determined, the position of the portion of the patient 16 can then be determined (e.g., via the processor 54) based on the relative spatial relationship between the marker block 202 and the patient 16. In some embodiments, by continuously determining the position of the portion of the patient 16 in real time, the portion of the patient 16 can be tracked in real time. The tracked position of the patient 16 may be used to gate an application of radiation provided by the system 10. In further embodiments, the tracked position of the patient 16 may be used to perform tracking of a target region while an intensity modulated radiation therapy (IMRT) is being performed. In IMRT, a multi-leaf collimator is operated such that a first portion of the target region receives more radiation than a second portion of the target region during a treatment session.

In further embodiments, the determined position of the marker block 202 can be used to determine a level of activity accomplished by the patient 16. For example, if the marker block 202 is placed on the patient's chest, then the determined position of the marker block 202 can be used to determine a level of breathing performed by the patient 16. In some cases, by determining a plurality of positions of the marker block 202 over a period of time, the processor 54 can be configured to obtain a plurality of amplitude points that correspond to the patient's levels of breathing at various time points in that period. The determined amplitude points may be used to gate an execution of a procedure, such as, to gate an application of a treatment radiation to the patient 16 for treatment, or to gate an application of an imaging radiation to the patient 16 for imaging purpose. In other embodiments, the determined positions of the marker block 202 (or the amplitude points) may be used to gate a binning of image data, either in real time, or after the image data has been obtained. In further embodiments, the amplitude points may be used to perform tracking of a target region while IMRT is being performed.

In further embodiments, by determining a plurality of positions of the marker block 202 over a period of time, the processor 54 can be configured to obtain a plurality of phase points that correspond to different levels of completeness of a breathing cycle at various time points. For example, a phase value may have a value from 0° to 360°, with 0° representing a beginning of a respiratory cycle, and 360° representing an end of the respiratory cycle. The determined phase values may be used to gate an execution of a procedure, such as, to gate an application of a treatment radiation to the patient 16 for treatment, or to gate an application of an imaging radiation to the patient 16 for imaging purpose. In other embodiments, the determined phase values may be used to gate a binning of image data, either in real time, or after the image data has been obtained. In further embodiments, the phase values may be used to perform tracking of a target region while IMRT is being performed.

One advantage to using the marker block 202 is that with a-priori knowledge of the relative positions of the reference locations 216 on the marker block 202, it is possible to determine all six degrees of freedom (X, Y, Z, $\theta_x$, $\theta_y$, $\theta_z$) of the marker block 202 from a single camera view. In other words, only a single camera is required to derive the absolute coordinates of a marker block 202. This results because the relative positioning between the markers 216 on the marker block 202 are known, and the absolute coordinates and viewing orientation of the camera 204 are also known. The detected image of the marker block 202 by the camera 204 indicates the positioning of the visible reference locations 216 relative to the camera's viewing orientation. Because the actual relative positions between the markers 216 are known, the detected relative coordinates of the markers 216 from the camera image can be used to derive the absolute coordinate of the marker block 202. The marker block 202 is also advantageous because its configuration allows the camera 204 to detect the markers 216 accurately.

Although the marker system 200 has been described as having one camera 204, in other embodiments, the marker system 200 can have more than one camera. For example, in alternative embodiments, the marker system 200 may include two cameras which detect the markers 216. In such cases, the processor 54 receives image data from the two cameras, and determine a position of the marker block 202 using triangulation technique, as is known in the art. Also, in other embodiments, instead of a camera, the marker system 200 may include other types of optical devices that are capable of detecting the markers 216.

Figure 5:
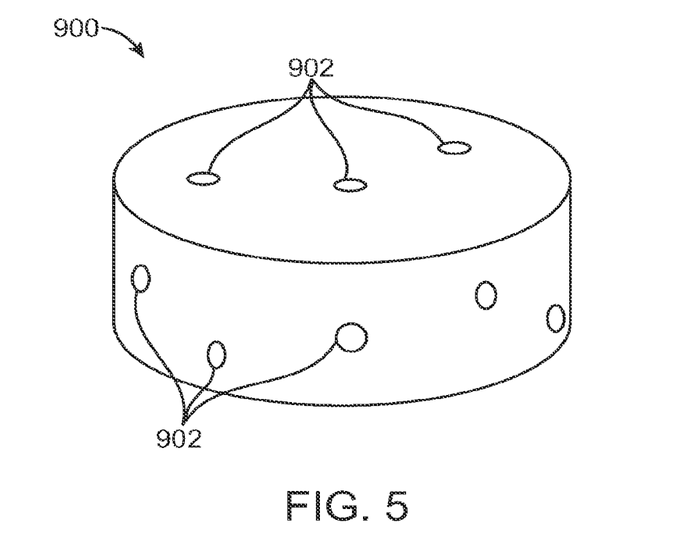
FIG. 5 illustrates a marker block in accordance with other embodiments.
Figure 6:
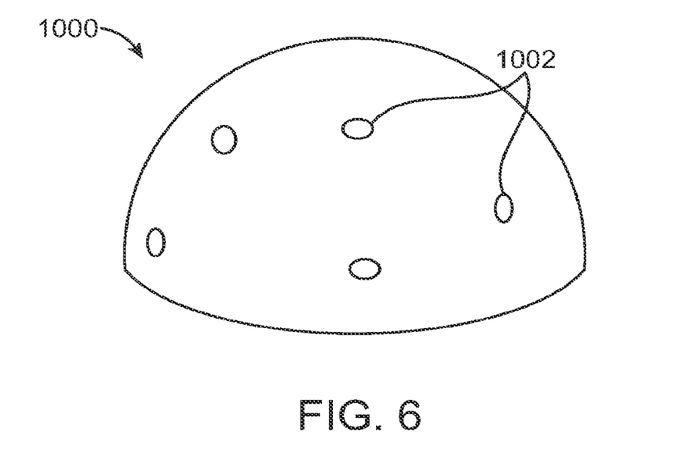
FIG. 6 illustrates a marker block in accordance with other embodiments.

In other embodiments, instead of the shape shown in the above examples, the marker block 202 can have different shapes. FIG. 5 depicts an embodiment of a marker block 202 having a cylindrical shape with multiple reference locations comprised of markers 216 located on its surface. FIG. 6 depicts an alternate marker block 202 having a hemispherical shape comprised of a plurality of markers 216 attached to its surface.

Figure 7:
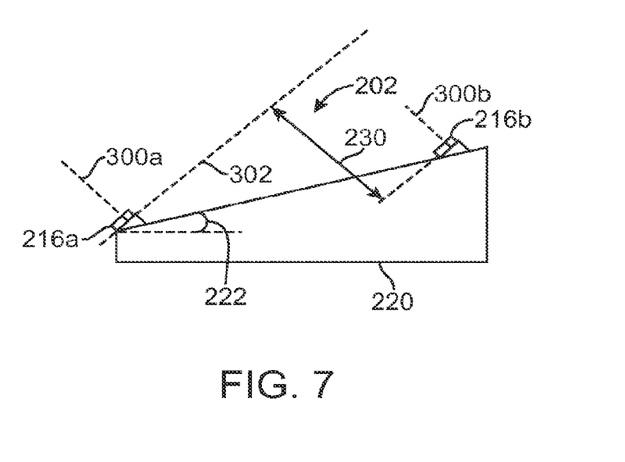
FIG. 7 illustrates a marker block in accordance with other embodiments.

FIG. 7 illustrates a variation of the marker block 202 in accordance with other embodiments. In the illustrated embodiments, the marker block 202 has a surface 212, and the markers 216a, 216b are located on the surface 212. The marker 216a has a normal 300a, and the marker 216b has a normal 300b. In some embodiments, each normal 300 is a vector that points towards a direction from which the marker 216 is intended to be viewed. Alternatively, each normal 300 may be defined as a vector that points towards a direction, onto which a projected area of the marker 216 is maximized. As shown in the figure, the normals 300a, 300b are parallel to each other. Alternatively, the normals 300a, 300b may form an angle that is less than 45°, and more preferably less than 25°.

In the illustrated embodiments, the marker 216b is spaced at a distance 230 from a plane 302 that intersects the marker 216a and that is perpendicular to the normal 300a. In such configuration, the markers 216a, 216b are spaced from each other. In some embodiments, the distance 230 is at least 0.5 centimeter, and more preferably at least 1.0 centimeter. Also as shown in the figure, the surface 212 forms an angle 222 with a base 220. In some embodiments, the angle 222 is selected such that the markers 216a, 216b are oriented approximately towards the camera 204. In other embodiments, the angle 222 may be predetermined without regards to the location of the camera 204. In such cases, when using the marker block 202, the camera 204 is positioned such that the markers 216a, 216b face approximately towards the camera 204. In some embodiments, the camera 204 is positioned relative to the marker block 202 such that a distance between the markers 216a, 216b measured in a viewing direction of the camera 204 is at least 0.5 centimeter, and more preferably at least 1.0 centimeter.

In other embodiments, the marker block 202 can be formed with shapes to fit particular body parts. For example, molds or casts that match to specific locations on the body can be employed as marker blocks 202. Marker blocks 202 shaped to fit certain areas of the body facilitate the repeatable placement of the marker blocks 202 at particular locations on the patient. Alternatively, the marker blocks 202 can be formed to fit certain fixtures that are attached to a patient's body. For example, a marker block 202 can be formed within indentations and grooves that allow it to be attached to eyeglasses. In yet another embodiment, the fixtures are formed with integral marker block(s) 202 having markers 216 on them.

In the above embodiments, the markers 216 are external to the patient 16. However, in alternative embodiments, the markers 216 may be placed inside the patient 16. In such cases, the marker block 202 is sized so that it can be placed in a target region within the patient 16. The markers 216 can be made from a material that is suitable for the imaging technique being employed to detect the markers 216. The detection of the markers 216 may be accomplished using any of the imaging techniques known in the art, such as, ultrasound imaging, CT imaging, fluoroscopy, and PET imaging.

In further embodiments, instead of the structure 210 being a non-human object, the structure 210 may be a portion of the patient 16. In such cases, the first surface 212 would be a first portion of the patient 16, the second surface 214 would be a second portion of the patient 16, and the markers 216 are then secured to, or placed on, the portions of the patient 16. For example, an ink marking may be placed on the patient 16 to function as the marker 216.

In further embodiments, the markers 216 may be portions of the patient 16. For example, landmarks on the patient 16 may be used as the markers 216.

Also, it should be understood by those skilled in the art that the marker system 200 can be used with different systems in different embodiments. For example, the radiation system 10 needs not be a treatment device, and may be any machine that is capable of generating a radiation beam. In some embodiments, the radiation system 10 may be any types of imaging or optical devices, such as a CT imaging device (e.g., a cone beam CT device), a laminar tomography machine, a MRI machine, a C-arm based x-ray imaging machine, a three dimensional angiography machine, or a PET machine. Also, in other embodiments, any of the marker systems 200 and/or methods described herein can be used with non-imaging devices, such as a positioner or a treatment machine that has no imaging capability. In further embodiments, any of the marker systems 200 and/or methods described herein can be used with a machine that has a plurality of radiation sources. For example, the machine can have a first radiation source for delivering diagnostic radiation (e.g., radiation having an energy level in the kilo-electron-volt range), and a second radiation source for delivering treatment radiation (e.g., radiation having an energy level in the mega-electron-volt range). As another example, the machine can also have a plurality of diagnostic radiation sources and/or one or more treatment radiation sources.

Computer System Architecture

Figure 9:
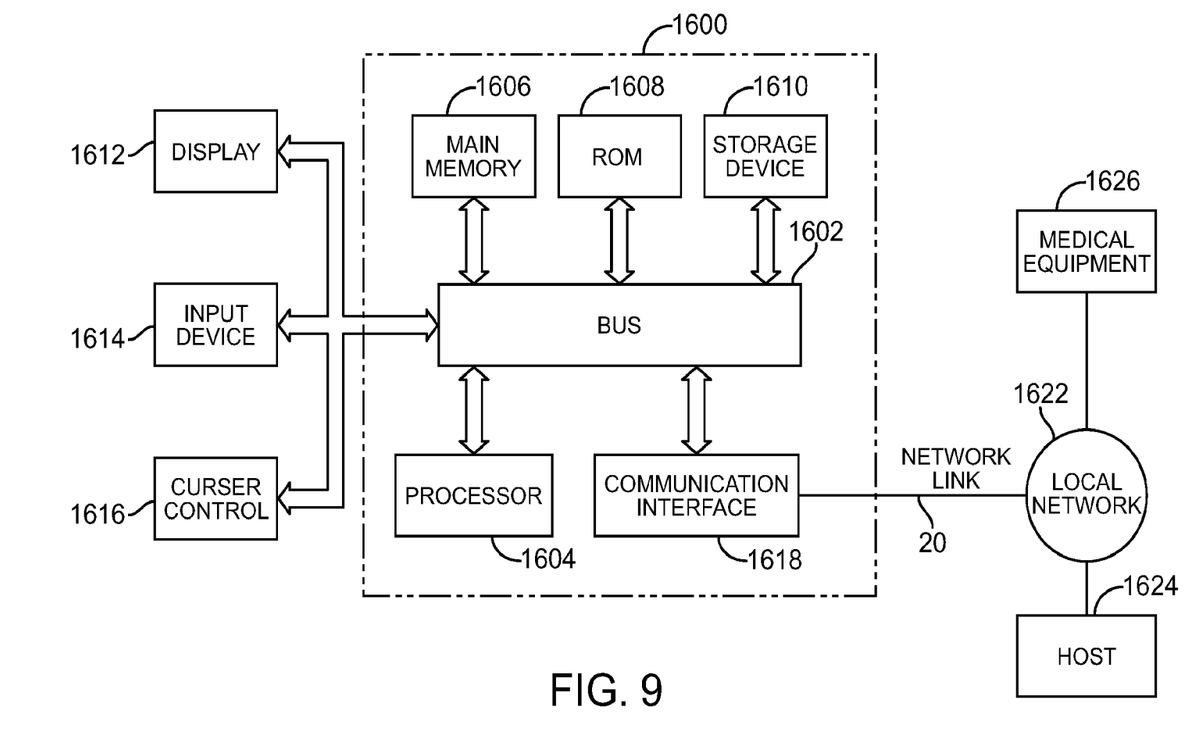
FIG. 9 illustrates a block diagram of a computer system with which embodiments described herein may be implemented.

FIG. 9 is a block diagram illustrating an embodiment of a computer system 1600 that can be used to implement various embodiments described herein. Computer system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. Volatile media includes dynamic memory, such as the main memory 1606. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network (s), the network link 1620, and the communication interface 1618.

Although particular embodiments have been shown and described, it will be understood that they are not intended to limit the present inventions, and it will be obvious to those skilled in the art that various changes and modifications may be made without departing from the spirit and scope of the present inventions. For example, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A marker system, comprising:
   a structure having a first surface, a second surface, and a third surface;
   a first marker coupled to the first surface; and a second marker coupled to the second surface;
wherein the first surface to which the first marker is coupled and the second surface to which the second marker is coupled are arranged so that their respective normals face approximately a same direction; and
wherein the first surface and the second surface are offset from each other at least in a direction along one of the normals, and the third surface is coupled between the first surface and the second surface.

2. The system of claim 1, wherein the first surface and the second surface are parallel.

3. The system of claim 1, wherein the first marker faces towards a first direction, the second marker faces towards a second direction, and the first and second directions do not vary by more than 15°.

4. The system of claim 1, further comprising a third marker on the first surface, and a fourth marker on the second surface.

5. The system of claim 1, further comprising a third marker on the first surface, and a fourth marker on the first surface.

6. The system of claim 1, wherein the first surface and the second surface face are separated by a distance having a value that is at least 0.5 centimeter.

7. The system of claim 1, further comprising a marking on the structure for indicating an orientation of the structure.

8. The system of claim 1, further comprising an optical device for viewing the first and the second markers.

9. The system of claim 8, further comprising a processor coupled to the optical device.

10. The system of claim 9, wherein the processor is configured to process data regarding a spacing between the first marker and the second marker, wherein the spacing is measured in a viewing direction of the optical device.

11. The system of claim 9, wherein the processor is configured to determine a position of the structure based at least in part on a relative spacing between the first marker and the second marker.

12. The system of claim 9, wherein the processor is configured to determine an orientation of the structure based at least in part on a relative spacing between the first marker and the second marker.

13. The system of claim 9, wherein the processor is configured to track a position of the structure.

14. The system of claim 1, wherein a distance between the first and the second surface measured in the direction along the one of the normals is at least 0.5 centimeter.

15. The system of claim 1, wherein the first surface has a planar region, the planar region having an area that is larger than an area of the first surface.

16. The system of claim 1, further comprising a first cross-marking on the third surface that is coupled between the first and second surfaces.

17. The system of claim 16, further comprising:
a fourth surface that is perpendicular to the third surface; and
a second cross-marking on the fourth surface.

18. The system of claim 1, wherein the first surface comprises a rectilinear surface.

19. A marker system, comprising:
a structure having a base, a first surface, a second surface, and a third surface coupled between the first surface and the second surface, the first surface forming an acute angle with the base, the angle being a value that is between 30° and 90°;
a first marker located on the first surface; and
a second marker located on the second surface;
wherein the first marker and the second marker face towards a direction, and are offset from each other along an axis that is parallel to the direction.

20. The system of claim 19, wherein the first surface and the second surface are parallel.

21. The system of claim 19, wherein the first surface and the second surface form an angle that is less than 45°.

22. The system of claim 19, further comprising a third marker on the first surface, and a fourth marker on the second surface.

23. The system of claim 19, further comprising a third marker on the first surface, and a fourth marker on the first surface.

24. The system of claim 19, wherein the first surface and the second surface face are separated by a distance having a value that is at least 0.5 centimeter.

25. The system of claim 19, further comprising a marking on the structure for indicating an orientation of the structure.

26. The system of claim 19, further comprising a camera for viewing the first and the second markers.

27. The system of claim 26, further comprising a processor coupled to the camera.

28. The system of claim 27, wherein the processor is configured to process data regarding a spacing between the first marker and the second marker, wherein the spacing is measured in a viewing direction of the camera.

29. The system of claim 27, wherein the processor is configured to determine a position of the structure based at least in part on a relative spacing between the first marker and the second marker.

30. The system of claim 27, wherein the processor is configured to determine an orientation of the structure based at least in part on a relative spacing between the first marker and the second marker.

31. The system of claim 27, wherein the processor is configured to track a position of the structure.

32. The system of claim 26, wherein a distance between the first and the second markers measured in a viewing direction of the camera is at least 0.5 centimeter.

33. The system of claim 19, further comprising a first cross-marking on the third surface that is coupled between the first and second surfaces.

34. The system of claim 33, further comprising:
a fourth surface that is perpendicular to the third surface; and
a second cross-marking on the fourth surface.

35. The system of claim 19, wherein the first surface comprises a rectilinear surface.

36. A marker system, comprising:
a structure having a first surface, a second surface, and a third surface coupled between the first surface and the second surface;
a first marker having a first normal, the first marker coupled to the first surface; and
a second marker having a second normal, the second marker coupled to the second surface;
wherein the first normal and the second normal form an angle that is less than 15°, and the second marker is spaced from a plane that is perpendicular to the first normal and that intersects the first marker; and
wherein the third surface has a first cross-marking that is located between the first marker and the second marker when viewed in a direction.

37. The system of claim 36, wherein the first marker and the second marker are arranged for simultaneous viewing by an optical device.

38. The system of claim 36, wherein the first surface is spaced from the second surface.

39. The system of claim 36, wherein the first marker and the second marker are separated by a distance having a value that is at least 0.5 centimeter, the distance measured in a direction of the first normal or the second normal.

40. The system of claim 36, wherein a distance between the first and the second markers measured in a viewing direction of a camera is at least 0.5 centimeter.

41. The system of claim 36, further comprising:
   a fourth surface that is perpendicular to the third surface; and
   a second cross-marking on the fourth surface.

42. The system of claim 36, wherein the first surface comprises a rectilinear surface.

\* \* \* \* \*

UNITED STATES PATENT AND TRADEMARK OFFICE
CERTIFICATE OF CORRECTION

| | | |
|---|---|---|
| PATENT NO. | : 8,417,315 B2 | Page 1 of 1 |
| APPLICATION NO. | : 11/748406 | |
| DATED | : April 9, 2013 | |
| INVENTOR(S) | : Hassan Mostafavi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1072 days.

Signed and Sealed this
Second Day of December, 2014

Michelle K. Lee
*Deputy Director of the United States Patent and Trademark Office*